United States Patent
Marwah et al.

(10) Patent No.: US 6,686,486 B1
(45) Date of Patent: *Feb. 3, 2004

(54) PROCESS FOR EFFECTING ALLYLIC OXIDATION

(76) Inventors: Padma Marwah, 229 Midvalle Blvd., Madison, WI (US) 53075; Henry A. Lardy, 1829 Thorstrand Rd., Madison, WI (US) 53705

(*) Notice: Subject to any disclaimer, the term of this patent is extended or adjusted under 35 U.S.C. 154(b) by 145 days.

This patent is subject to a terminal disclaimer.

(21) Appl. No.: 09/639,027

(22) Filed: Aug. 14, 2000

Related U.S. Application Data

(63) Continuation of application No. 09/228,902, filed on Jan. 11, 1999, now Pat. No. 6,111,118, which is a continuation-in-part of application No. 08/851,939, filed on May 7, 1997, now Pat. No. 5,869,709.

(51) Int. Cl.$^7$ .............. C07J 1/00; C07J 45/00; C07J 21/00; C07C 9/00
(52) U.S. Cl. ............ 552/615; 552/542; 504/31; 568/232; 568/326; 560/129
(58) Field of Search .............. 552/615, 542; 540/31; 568/232, 326; 560/129

(56) References Cited

U.S. PATENT DOCUMENTS

| | | | |
|---|---|---|---|
| 3,914,295 A | | 10/1975 | Rosenthal et al. |
| 4,263,215 A | * | 4/1981 | Hesse et al. .............. 260/397.2 |
| 4,554,105 A | * | 11/1985 | Hesse .............. 260/397.2 |
| 4,659,829 A | | 4/1987 | Saussine et al. |
| 5,030,739 A | | 7/1991 | Foricher et al. |
| 5,296,481 A | | 3/1994 | Partridge et al. |
| 5,354,919 A | | 10/1994 | Costantini et al. |
| 5,457,111 A | | 10/1995 | Luly et al. |
| 5,585,371 A | | 12/1996 | Lardy |
| 5,869,709 A | * | 2/1999 | Marwah et al. .............. 552/615 |
| 6,111,118 A | * | 8/2000 | Marwah et al. .............. 552/615 |

FOREIGN PATENT DOCUMENTS

| | | |
|---|---|---|
| WO | WO 95/32215 | 11/1995 |
| WO | WO 96/12810 | 5/1996 |
| WO | WO 97/37664 | 10/1997 |

OTHER PUBLICATIONS

Dictionary of Steroids, *Chapman & Hall*, p. 509–510 (1991).
Summary of the Invention, WO 95/32215, p. 2 (1995).
Amann, et al., "Stereospecific Syntheses of the Four Epimers of 7,22–Dihydroxycholesterol," *Synthesis*, p. 1002–1005 (1987).
Barton, et al., "Metal Dependence in Gif–type Reactions. The Cu(II)–catalyzed Olefination of Saturated Hydrocarbons by tert–Butyl Hydroperoxide," *Tetrahedron Letters*, 34(4):567–570 (1993).
Bulman Page, et al., "Oxidation Adjacent to C=C Bonds," *Comprehensive Organic Synthesis*, 7:83–84, 99–117 (1991).

Cheng, et al., "Chemistry and Biochemistry of Chinese Drugs. Part I. Sterol Derivatives Cytotoxic to Hepatoma Cells, Isolated from the Drug," *J. Chem. Research* p. 217 (1977).
Chidambaram, et al., "tert–Butyl Hydroperoxide–Pyridinium Dichromate: A Convenient Reagent System Allylic and Benzylic Oxidations," *J. Org. Chem.*, 52(22):5048–5051 (1987).
Dauben, et al., "Allylic Oxidation of Olefins with Chromium Trioxide–Pyridine Complex," *J. Org. Chem.*, 34(11):3587–3592 (1969).
Dodson, et al., "Microbiological Transformations. IV. The Oxidation of Dehydroepiandrosterone at C–7," 81:6295–6297 (1959).
Feldberg, et al., "Copper–catalysed Oxidation of Hydroxy Compounds by tert–Butyl Hydroperoxide Under Phase–transfer Condiditons," *J. Chem. Soc., Chem. Commun* p. 1807 (1994).
Fieser, Louis R., "Preparation of Ethylenethioketals," 76:1954–1947 (1954).
Fullerton, et al., "In Situ Allylic Oxidations with Collins Reagent," *Synthetic Communications*, 6(3):217–220 (1976).
Hudlicky, Milos, "Derivatives of Group 6 Elements," *Oxidants in Organic Chemistry*, p. 20–21.
Lardy, et al., "Ergosteroids II: Biologically Active Metabolites and Synthetic Derivatives of Dehydroepiandrosterone," *Steroids*, 63(3):158–165 (1998).
Kawasaki, et al., "Enantioselective Allylic Oxidation Using Biomimetic Tris(oxazolines)–Copper(II) Complex," *Synlett*, 12:1245–1246 (1995).
Kimura, et al., "On the Reactions of Cholesteryl Acetate with tert–Butyl Hydroperoxide in the Presence of Tris(acetylacetonato)iron(III)," *Chem. Pharm. Bull.*, 27(1):109–112 (1979).
Kimura, et al., "The Reactions of Cholesteryl Acetate with Various Hydroperoxides in the Presence of Tris(acetylacetonato)iron(III) and Hexacarbonylmolybdenum," *Chem. Pharm. Bull.*, 28(6):1836–1841 (1980).
Kumar, et al., "Stereospecific Synthesis of 7β–Hydroxycholesterols," *Synthetic Communications*, 28(6):1836–1841 (1980).
Marshall, et al., "7–Keto Steroids. II. Steroidal 3β–and Delta5–7–ones and Delta3,5–7–Ones," *J. Am. Chem. Soc.*, 79:6308–6313 (1957).

(List continued on next page.)

*Primary Examiner*—Alton N Pryor
(74) *Attorney, Agent, or Firm*—Heather L. Callahan

(57) ABSTRACT

A procedure for oxidizing organic compounds having allylic hydrogen atom(s) involving the steps of reactively contacting the organic compound with a combination of a periodic acid or metal periodate and an alkyl hydroperoxide under conditions of normal as well as elevated pressure of a suitable gas like air. The reaction can conveniently be conducted at temperatures between about 0–65° C. in a cosolvent system of water and organic solvent(s).

42 Claims, No Drawings

OTHER PUBLICATIONS

Marwah, et al., "Steroidal Allylic Fluorination Using Diethylaminosulfur Trifluoride: A Convenient Method for the Sythesis of 3β acetoxy–7α– and 7β–fluoroandrost–5–en–17–one," *Steroids*, 61:453–460 (1996).

Miller, et al., "A Ruthenium Catalyzed Oxidation of Steroidal Alkenes to Enones," *Tetrahedron Letters*, 37(20):3429–3432 (1996).

Muzart, "Synthesis of Unsaturated Carbonyl Compounds via a Chromium–Mediated Allylic Oxidation by 70% Tert-.Butylhydroperoxide," *Tetrahedron Letters* 28(40):4665–4668 (1987).

Nagano, et al., "Chemistry and Biochemistry of Chinese Drugs. Part II. Hydroxylated Sterols, Cytoxic Towards Cancerous Cells: Synthesis and Testing," *J. Chem. Research* p. 218 (1977).

Parish, et al., "Allylic Oxidation of Δ5–Steroids with Pyridinium Chlorochromate (PCC) and Pyridinium Dichromate (PDC)," *Synthetic Comm.* 17(10):1227–1233 (1987).

Parish, et al., "Pyridinium Chlorochromate–Mediated Allylic and Benzylic Oxidation," *Synthetic Comm.* 16(11):1371–1375 (1986).

Pearson, et al., "A New Method for the Oxidation of Alkenes to Enones. An Efficient Synthesis of Δ5–7–Oxo Steroids," *Chem. Soc. Perkin Trans. I*, p. 267–273 (1985).

Pearson, et al., "Oxidation of Alkenes to Enones Using tert–Buytl Hydroperoxide in the Presence of Chromium Carbonyl Catalysts," *Tetrahedron Letters*, 25(12):1235–1238 (1984).

Salmond et al., "Allylic Oxidation with 3,5–Dimethylpyrazole. Chromium Trioxide Complex. Steroidal 5–7 Ketones," *J. Org. Chem.*, 43(10):2057–2059 (1978).

Salvador, et al., "Copper–Catalysed Allylic Oxidation of 5–Steroids by t–Butyl Hydroperoxide," *Tetrahedron Letters*, 38(1):119–122 (1997).

Sato, et al., "Oxygenated Sterols as Inhibitors of Enzymatic Conversion of Dihydrolanosterol into Cholesterol," *Chem. Pharm. Bull.*, 32(8):3305–3308 (1984).

Singh, "Phase–transfer Catalyzed Allylic Oxidation of Hindered Double Bonds in a Rigid Framework by Sodium Periodate," *Indian J. of Chem.*, 24B:859 (1985).

Zondervan, et al., "Remarkable Reversal of the Non–linear Effect in the Catalytic Enantioselctive Allylic Oxidation of Cyclohexene Using Copper Proline Complexes and t–Butyl Hydroperoxide," *Tetrahedron:Asymmetry*, 7(7):1895–1898 (1996).

* cited by examiner

US 6,686,486 B1

PROCESS FOR EFFECTING ALLYLIC OXIDATION

CROSS-REFERENCES TO RELATED APPLICATIONS

This Application is a continuation of prior application Ser. No. 09/228,902, filed Jan. 11, 1999 (Issued as U.S. Pat. No. 6,111,118), which is a continuation in part of prior application Ser. No. 08/851,939 filed May 7, 1997 (Issued as U.S. Pat. No. 5,869,709), both of which are hereby incorporated by reference herein in their entirety including any drawings, figures, or tables.

FIELD OF THE INVENTION

The invention relates to the allylic oxidation of organic compounds.

BACKGROUND

Allylic oxidation is a fundamental organic reaction of significant interest to organic chemists practicing in a variety of fields from agricultural products to pharmaceuticals. A variety of procedures are known for oxidizing various organic compounds that possess allylically activated hydrogen, but such procedures typically suffer from unsatisfactory yields, tedious workups and/or require the use of expensive and/or ecologically and physiologically undesirable reagents, such as chromium.

Hence, a continuing need exists for a simple, efficient, safe and cost-effective procedure for selectively effecting allylic oxidation of organic compounds.

SUMMARY OF THE INVENTION

We have discovered a simple, efficient, safe, cost-effective and ecologically friendly procedure for oxidizing organic compounds having allylic hydrogen atom(s). The procedure involves reactively contacting the organic compound with a combination of periodic acid or metal periodate and an alkyl hydroperoxide under conditions sufficient to effect oxidation of the allylic hydrogen(s) on the organic compound.

The reaction is conveniently conducted in a cosolvent system of water and organic solvent(s), and is usually conducted at ambient temperature and normal pressure conditions. However, the yield of the desired product can generally be further improved and/or the reaction process facilitated by conducting the reaction under increased pressure and/or above ambient temperature.

DETAILED DESCRIPTION OF THE INVENTION INCLUDING A BEST MODE

Definitions

As utilized herein, including the claims, the term "allylic compound" references an organic compound having at least one allylic hydrogen atom.

As utilized herein, including the claims, the term "allylic oxidation" means oxidation of an allylic compound by replacing the allylic hydrogen(s) with oxygen or an oxygen containing group.

As utilized herein, including the claims, the term "reactants" collectively references allylic compound, periodic acid or metal periodate and alkyl hydroperoxide. Solvents, including both organic solvent(s) and water, are specifically excluded from the definition of reactants.

As utilized herein, including the claims, "(v/v)" refers to the volumetric percentage of water to total water miscible solvent(s).

Process

The process involves reactively contacting an allylic compound with a metal periodate or periodic acid and an alkyl hydroperoxide under conditions of normal to increased pressure of air or nitrogen and/or zero to above ambient temperature to effect allylic oxidation of the allylic hydrogen atom(s) on the organic compound. For example, the allylic compound can be allylically oxidized by (i) dissolving the allylic compound in a suitable mixture of a water miscible organic solvent, a water immiscible organic solvent and the alkyl hydroperoxide, (ii) incorporating the periodic acid or metal periodate and a suitable amount of water into the reaction mixture, and then (iii) optionally pressurizing the reaction vessel with air or nitrogen. In the case of metal periodates, water gradually dissolves the periodate during the course of the reaction and thereby provides the necessary reactive contact between the reactants. As an added feature, the limited solubility of metal periodate in water permits the pH of the reaction mixture to be controlled to some extent should such pH control be desired.

CONSTITUENTS

Allylic Compounds

Allylic compounds include any organic compound incorporating the structure $-C^1R \equiv C^2H-C^3H_n-$ within the molecule, wherein n is 1, 2 or 3. Hydrogen atoms attached to the $C^1$ and $C^2$ carbon atoms are referenced as vinylic hydrogen. Hydrogen atoms attached to the $C^3$ carbon atom are referenced as allylic hydrogen. The process of this invention selectively oxidizes allylic hydrogen atoms over vinylic hydrogen atoms. Exemplary allylic compounds include specifically, but not exclusively, (i) aliphatic vinylic compound such as methyl oleate, (ii) aromatic benzylic compounds such as fluorene and diphenyl methane, (iii) isoprenoids, such as carotenoids, terpenes, sesquiterpenes and vitamins, and (iv) steroids and sterols, such as androstenes, cholesterol, estraenes, pregnenes and derivatives thereof such as esters, ethers and ketals of these compounds.

Of particular commercial interest is the allylic oxidation of steroids, such as dehydroepiandrosterone and various derivatives of dehydroepiandrosterone, because the steroid can be allylically oxidized without the use of physiologically or ecologically hazardous materials, such as the transition metals. The invention does not contaminate the allylically oxidized product with a toxic metal.

Cooxidants (Periodic Acid, Metal Periodate and Alkyl Hydroperoxide)

A cooxidant system of a metal periodate or a periodic acid and an alkyl hydroperoxide is used to allylically oxidize the allylic compound. The term metal periodates references salts of periodic acid with monovalent alkali metals such as sodium, divalent metals such as zinc or transition metals like iron. The required salts may be generated in the reaction in-situ, if required, by the addition of commonly available salts of the metals such as zinc acetate, ferric chloride, etc. Experimentation has shown that the specific combination of sodium periodate and butyl hydroperoxide can generally provide a superior yield and/or superior quality of allylically oxidized product under ambient reaction conditions, which can further be improved by conducting the reaction under slightly increased pressure of air or nitrogen and slightly above ambient temperature. An additional benefit provided by the use of butyl hydroperoxide is that butyl hydroperoxide is a liquid under ambient conditions and can also facilitate dissolution of the allylic compound in the organic solvent(s).

The metal periodate, periodic acid and alkyl hydroperoxide reactants are available from a number of chemical suppliers. The alkyl hydroperoxide can be conveniently utilized as an aqueous solution or even in its anhydrous form. Since the reaction mixture preferably includes water for the purpose of gradually dissolving the metal periodate during the course of the reaction, the alkyl hydroperoxide is most conveniently utilized as a 70–90 wt % aqueous solution.

Generally, a concentration of about 0.5 to about 5 mole equivalents of periodic acid or metal periodate, preferably about 1.0 to about 3 mole equivalents of periodic acid or metal periodate, and about 10 to about 15 mole equivalents of alkyl hydroperoxide are effective for allylically oxidizing an allylic compound. Concentrations of less than about 0.5 mole equivalent of periodic acid or metal periodate and less than about 10 mole equivalents of alkyl hydroperoxide significantly slows the reaction, while greater than about 3 mole equivalents of periodic acid or metal periodate and greater than about 15 mole equivalents of alkyl hydroperoxide increases the cost of the process without producing a corresponding increase in any beneficial property or characteristic of the process or resultant product(s).

Organic Solvent(s)

The organic reactants (i.e., allylic compound and alkyl hydroperoxide) can be conveniently dissolved in suitable organic solvent(s). Depending upon the specific allylic compound and alkyl hydroperoxide used, the organic compounds may be suitably dissolved in a water miscible organic solvent(s), or may require the use of a biphasic organic solvent system which includes at least one water miscible organic solvent and at least one water immiscible organic solvent.

The water miscible solvent, when utilized, is selected primarily for its ability to dissolve the organic reactants and in a biphasic system, to facilitate reactive contact between the water soluble periodic acid or metal periodate and the organic reactants solubilized in the water immiscible organic solvent. Suitable water miscible organic solvents include specifically, but not exclusively, acetone, acetonitrile, t-butanol and organic bases such as pyridine.

The water immiscible solvent, when utilized, is selected primarily for its ability to dissolve the specific allylic compound to be oxidized and to create a clear biphasic reaction mixture. A variety of suitable water immiscible solvents are available, including specifically, but not exclusively: (i) aliphatic hydrocarbons, such as petroleum ether, n-hexane, n-heptane and isooctane, and (ii) alicyclic hydrocarbons, such as cyclohexane, (iii) aliphatic alkyl esters such as ethyl acetate, and (iv) helogenated hydrocarbons such as methylene dichloride.

Water

A sufficient amount of water is preferably incorporated into the reaction mixture for the purpose of controllably dissolving the metal periodate throughout the course of the reaction. As previously referenced, the limited solubility of metal periodate in water permits the pH of the reaction mixture to be controlled to some extent in those situations where pH control is necessary or desirable.

The reaction mixture can conveniently incorporate about 10% to about 50% (v/v), preferably about 15% to about 40% (v/v), most preferably about 20% to about 30% (v/v), water. A concentration of less than about 10% (v/v) significantly slows the rate of reaction, with a complete absence of water resulting in an almost complete absence of any allylic oxidation of the allylic compound specifically in the case of oxidants involving use of metal periodates.

SOLID SUPPORT

Although the reaction is primarily conducted in an organic solvent in a single phase or in a biphasic reaction mixture involving use of a water immiscible solvent, it can also be conducted conveniently using metal periodate or periodic acid on a solid support. For this purpose, the metal periodate or periodic acid is ground in a suitable grinding device along with a solid support material. The solid support material may be selected from such commercially available support materials as alumina, silica gel, bentonite, celite, etc. In general, the ground metal periodate or periodic acid should constitute about 20% to about 60% of the solid support, more preferably about 20% to about 40% of the solid support, and most preferably about 50% of the solid support. The use of solid supports does not necessarily result in an increased yield, but does simplify work up of the reaction mixture.

PROCESSING PARAMETERS AND PROCEDURES

Reaction Time

While dependent upon a number of variables, including the specific allylic compound being oxidized, the specific cooxidants being used and the concentration of reactants within the reaction mixture, the reactions can typically be conducted in about 6 to about 48 hours.

Reaction Temperature

The reaction can normally be conducted at ambient or slightly sub-ambient conditions (i.e., temperatures between about 0–25° C.). We have found that reaction time can be drastically reduced by conducting the reaction at elevated temperatures of between 35–65° C., preferably about 40° C.

In addition, we have found that the formation of $\Delta 5$-androsterone-4,7-dione derivatives, a common contaminant obtained during the oxidation of dehydroepiandrosterone derivatives, can be drastically reduced by conducting the oxidation at above ambient temperature.

Reaction Pressure

We have found that an increased yield can be obtained by conducting the reaction under conditions of elevated pressure using a suitable gas such as air or nitrogen (i.e., a pressure of greater than 1 atmosphere). The reaction is preferably conducted at a pressure of about greater than 1 to 10 atmospheres, more preferably at a pressure between 2 to 5 atmospheres, and most preferably at about 3 atmospheres. Suitable gases include air, nitrogen and combinations thereof.

A continuing increase in total yield of the product is generally observed up to a pressure of about 3 atmospheres, with pressures above about 10 atmospheres substantially increasing the cost of the processing equipment without a corresponding increase in yield. While the specific increase in yield attributable to elevated pressure depends upon a number of variables, including the specific reactants involved in the reaction, as a general matter we have found that an increase of up to 10% in total yield can be achieved.

pH

The pH of the reaction mixture can impact the yield of desired product, with the optimal pH primarily dependent upon the specific allylic compound being oxidized. Periodic acid or metal periodates are acidic reagents which tend to acidify the reaction mixture to a pH of approximately 1 to 5 depending upon the specific oxidant being used. In those cases where a more neutral pH is desired, such as when the allylic compound includes an acid sensitive group(s), the normally acidic pH of the reaction mixture can be neutralized to some extent by incorporating an organic base, such as pyridine, or a weak inorganic base, such as sodium bicarbonate, into the reaction mixture. Alternatively, the reaction can be conveniently carried out by using a solvent system of water and a water miscible organic base, such as pyridine.

Mixing

The reaction mixture should be continuously and vigorously stirred in order to promote contact between the reactants dissolved within the various solvents and thereby enhance the yield and/or quality of the desired allylically oxidized organic compound. In the absence of active mixing, we have observed a significant decrease in the yield and the quality of the desired product.

Solvent Dilution Factor

As with substantially any solvent-based reaction, the wt % solids should be retained between an upper solubility limiting percentage and a lower reaction rate limiting percentage. As the upper wt % of solids is reached, the viscosity of the resultant reaction mixture increases to such an extent that the necessary molecular interaction of the reactants are limited (e.g., the reaction mixture cannot be effectively mixed, with a resultant loss in yield and/or increased reaction time). Conversely, as the lower wt % of solids is reached, the reaction time begins to increase dramatically due to the reduced opportunity for the reactants to encounter one another within the reaction mixture. Such low concentrations of solids also results in increased expense due to the excessive amounts of solvent used per unit of reaction product obtained.

While the preferred wt % of solids in the reaction mixtures of this invention depend upon a number of variables, including the specific solvent(s) used and the specific reactants employed, a solids wt % of between about 5 wt % to about 15 wt % has been found to be generally acceptable for producing a high yield of good quality product at a reasonable rate of reaction.

Separation and Purification Techniques

Upon completion of the oxidation reaction, the oxidized allylic organic compound can be separated from the solvent system, as well as any unused reactants and any byproducts, by any of a variety of techniques known to those skilled in the art including dilution, filtration, extraction, evaporation, distillation, decantation, crystallization/recrystallization, chromatography, etc.

The excess of alkyl hydroperoxide present in the system can be decomposed, when desired, by methods known to those skilled in the art, such as (i) adding an aqueous solution of an alkali metal sulfite, (ii) adding a mixture of a mineral acid and acetic acid at sub-ambient temperatures (e.g., 0–5° C.), or (iii) adding a solution of a transition metal salt (e.g., ferrous ammonium sulfate in water).

The separated oxidized allylic organic compound can be further purified by various known techniques such as (i) washing the separated oxidized allylic organic compound with a solvent effective for selectively dissolving any remaining contaminants without dissolving appreciable quantities of the oxidized allylic organic compound, such as water or diethyl ether, and/or (ii) crystallizing the separated oxidized allylic organic compound in a suitable solvent or cosolvents.

In the case of allylic oxidation of steroids such as dehydroepiandrosterone derivatives, the product is often contaminated with trace amounts of the corresponding 4,7-dione derivatives, which has proven difficult to remove by usual techniques such as crystallization. Hence, dehydroepiandrosterone derivatives produced in accordance with the process are best purified by treating the crude product with weak inorganic bases such as bicarbonates, or with inorganic adsorbents like alumina in an organic solvent such as a lower ketone like acetone, halogenated hydrocarbon like methylene dichloride, lower aliphatic esters like ethyl acetate, lower alkanol like methanol or a suitable combination thereof.

EXAMPLES

Example 1

(Oxidation of 3β-Acetoxyandrost-5-ene-17-one (DHEAAc) to 3β-Acetoxyandrost-5-ene-7,17-dione (7-oxo-DHEAAc))

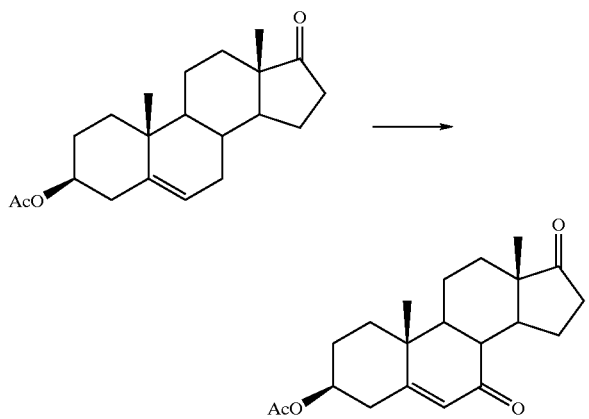

OXIDATION

3β-Acetoxyandrost-5-ene-17-one (DHEAAC) (50.0 grams, 0.15 mol) was dissolved in a mixture of acetone (350 ml), petroleum ether (350 ml) and t-butyl hydroperoxide (70% aqueous solution, 200 ml). The solution was stirred vigorously at room temperature and sodium periodate (42.6 grams, 0.2 mol) and water (90 ml) added. After 16 hours of continuous stirring, an additional amount of sodium periodate (10.7 grams, 0.05 mol) and water (20 ml) were added and the reaction mixture stirred continuously until the reaction had run to completion (TLC; Total 20 to 24 hours).

SEPARATION

The reaction mixture was then poured with stirring into a mixture of ice water (3000 ml) and ethyl acetate (100 ml) and stirred for 1 hour, after which the mixture was suction filtered. The white crystalline solid material was washed thoroughly with water and dried under vacuum, yielding 29 grams of technical 7-oxo-DHEAAc having a melting point of 182–184° C.

SECONDARY RECOVERY

The organic layer of the mother liquor was separated in a separatory funnel, washed well with water, and the solvent distilled off under reduced pressure. The resultant oily mass was dissolved in glacial acetic acid (100 ml) and cooled to 0–5° C. Perchloric acid (60% solution, 2 ml) was added dropwise to the cooled solution and the solution stirred at this temperature for 15 minutes, after which it was poured into ice water. The aqueous layer was extracted with an ethyl acetate/petroleum-ether solvent system (2:1). The resultant organic phase was washed well with water and distilled. The residue was taken up in diethyl ether (100 ml) and held for 2 hours at −20° C. to form a crystalline precipitate. The crystalline material was filtered, washed with cold ether, and dried under suction to give an additional amount (6.2 grams) of 7-oxo-DHEAAc having a melting point of 182–184° C.

YIELD

Total combined yield of 7-oxo-DHEAAc was 35.2 grams (68.2%).

PURIFICATION AND CHARACTERIZATION

The total combined yield of 7-oxo-DHEAAc (35.2 grams) was recrystallized from methanol-water (300 ml, 5:1) to yield 30.0 grams (58.14%) of pure crystalline 7-oxo-DHEAAc as white needles having a melting point of 185–187° C. and the following NMR spectrum.

$^1$H NMR (CDCl$_3$, 200 MHz): δ 5.76 (d, J=1.4 Hz, 1H, 6H), 4.73 (m, 1H, 3α-H), 2.06 (s, 3H, COCH$_3$), 1.24 (s, 3H, 19-CH$_3$), 0.90 (s, 3H, 18-CH$_3$).

SIDE PRODUCTS

The organic filtrate was evaporated and chromatographed on silica gel (200–400 mesh) using ethyl acetate-petroleum ether as eluent. The side products identified below in Table 1 were isolated from the filtrate. The quantities of each side product are also listen below in Table 1.

TABLE 1

| NUMBER | QUANTITY (%) | FORMULA | SPECTRAL DATA |
|---|---|---|---|
| 1 | 3 | | $^1$H NMR(CDCL$_3$, 200 MHz) δ 5.7(s. 6,7-H), 5.2(m, 3α-H), 2.03(s, COCH$_3$), 1.17(s, t-CMe$_3$), 0.97(s, 19-CH$_3$), 0.92(s, 18-CH$_3$); Mass: m/e 358(M—CH$_3$COOH), 329 (M—OOtBu), 269(M—CH$_3$COOH, OOtBu), 270(M—CH$_3$COO, OOtBu). |
| 2 | 5 | | $^1$H NMR(CDCL$_3$): δ 5.68(d, J=4.8, 6-H), 4.68(m, 3α-H), 4.25(t, J=4.6, 7β-H), 2.047 (s, COCH$_3$), 1.21(s, t-CMe$_3$), 1.01(s, 19-CH$_3$), 0.86(s, 18-CH$_3$); Mass: m/e 329, 302 (M—CH$_3$COOH, CO, CH$_2$=CH$_2$), 269, 270. |
| 3 | 5 (α 10%) (β 90%) | | $^1$H NMR(CDCL$_3$): δ 4.78(m, 3α-H), 3.15 (d, J=2.4Hz, 6-H), 2.037(s, COCH$_3$), 1.04 (s, 19-CH$_3$), 0.85(s, 18-CH$_3$), in case of α-epoxide 6-H comes at δ 3.5 J=4.64Hz. |
| 4 | 2–5 a (α 30%) b (β 70%) | | $^1$H NMR(CDCL$_3$): δ 8.25(OOH, 4a), 8.08 (OOH, 4b), 5.74(d, J=6.2, 6-H(4a), 5.64(t, J=1.6Hz, 6-H(4b)), 4.67(m, 3α-H), 4.28(dt, J=8.8, 2.0Hz, 7-H), 2.05(s, COCH$_3$), 1.09 (s, 19-CH$_3$(4b)), 1.03(s, 19-CH$_3$(4a), 0.9(s, 18-CH$_3$(4b)), 0.88(s, 18-CH$_3$(4a)). |
| 5 | 10–15 | | $^1$H NMR(CDCL$_3$): δ 5.66(d, J=4.8, 6-H), 4.63(m, 3α-H), 3.97(t, J=4.4Hz, 7β-H), 2.05(s, COCH$_3$), 1.04(s, 19-CH$_3$), 0.89(s, 18-CH$_3$). |

Example 2

(Oxidation of 3β-Acetoxyandrost-5-ene-17-one (DHEAAc) to 3β-Acetoxyandrost-5-ene-7,17-dione (7-oxo-DHEAAc))

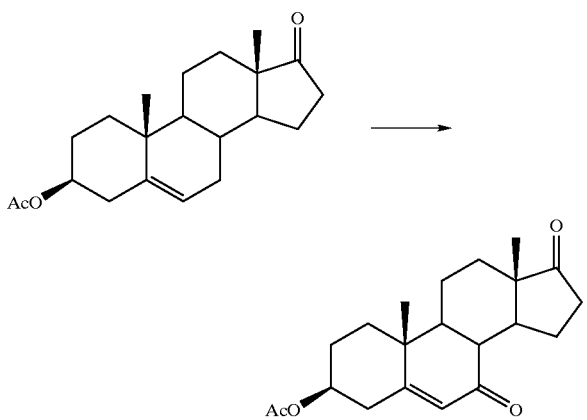

OXIDATION

3β-Acetoxyandrost-5-ene-17-one (DHEAAc) (3.3 grams, 0.01 mol) was dissolved in a mixture of acetone (40 ml) and anhydrous t-butyl hydroperoxide (3M solution in 2,2,4-trimethylpentane, 50 ml). The solution was stirred vigorously at room temperature and sodium periodate (10 grams, 0.046 mol) and water (10 ml) added. This biphasic reaction mixture was stirred continuously until the reaction had run to completion (16 hours).

SEPARATION

The reaction mixture was filtered through a bed of celite and acetone was removed from the residue under reduced pressure. The residue was dissolved in dichloromethane, washed with water and stirred with an aqueous sodium sulfite solution (10% aqueous solution, 50 ml) for 1 hour at room temperature. The organic layer was separated, washed with water, dried over anhydrous magnesium sulfate and solvent removed by distillation to form a crude material. The crude material was stirred with ether to afford a white crystalline material (2.2 grams).

SECONDARY RECOVERY

The mother liquor was chromatographed on silica-gel (70–230 mesh) using ethyl acetate-hexane (3:1) as eluent to yield an additional amount (0.3 gram) of 7-oxo-DHEAAc.

YIELD

Total combined yield of 7-oxo-DHEAAc was 2.5 grams (72.7%).

PURIFICATION AND CHARACTERIZATION

The 7-oxo-DHEAAc (2.5 grams) was recrystallized from methanol-water (9:1) to yield 2.2 grams (63.95%) of pure crystalline 7-oxo-DHEAAc as white needles having a melting point of 185–187° C.

Example 3

(Oxidation of 3β-Acetoxyandrost-5-ene-17-one (DHEAAc) to 3β-Acetoxyandrost-5-ene-7,17-dione (7-oxo-DHEAAc))

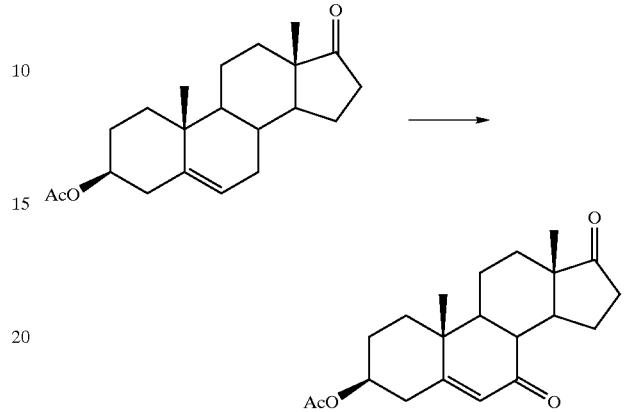

OXIDATION

3β-Acetoxyandrost-5-ene-17-one (DHEAAc) (3.3 grams, 0.01 mol) was dissolved in a mixture of t-butanol (35 ml), isooctane (35 ml) and t-butyl hydroperoxide (70% aqueous solution, 20 ml). The solution was stirred vigorously at room temperature and sodium periodate (6.62 grams, 0.03 mol) and water (9 ml) added. This biphasic reaction mixture was stirred continuously for 24 hours, at which time approximately 90% of the DHEAAc had reacted.

SEPARATION

The organic solvent was distilled off and the residue poured into ice water (200 ml), extracted with dichloromethane (30 ml), washed with water, dried and distilled to remove solvent. The residue was dissolved in diethyl ether (30 ml) and held for 2 hours at −20° C. to form a crystalline precipitate. The crystalline material was filtered, washed with cold ether, and dried under suction to yield 1.5 grams of 7-oxo-DHEAAc.

SECONDARY RECOVERY

The ethereal filtrate was shaken with a sodium sulfite solution (15% aqueous solution, 100 ml) for 2 hours at room temperature. The ether layer was separated from the solids, washed with water, dried and the solvent removed under suction. The resulting residue was dissolved in methanol (10 ml), held at −20° C. for 4 hours and filtered. The solids were filtered to yield another 0.35 gram of 7-oxo-DHEAAc. It is noted that the residue could have alternatively been purified by column chromatography on silica gel (70–230 mesh) using hexane-ethyl acetate (3:1) as eluent.

YIELD

Total combined yield of 7-oxo-DHEAAc was 1.85 grams (59.7% based upon 90% conversion).

PURIFICATION AND CHARACTERIZATION

The 7-oxo-DHEAAc (1.85 grams) was recrystallized from acetone-hexane to yield 1.75 grams (56.5% based upon 90% conversion) of pure crystalline 7-oxo-DHEAAc as white needles having a melting point of 184–186° C.

Example 4

(Oxidation of 3β-Acetoxyandrost-5-ene-17-one (DHEAAc) to 3β-Acetoxyandrost-5-ene-7,17-dione (7-oxo-DHEAAc))

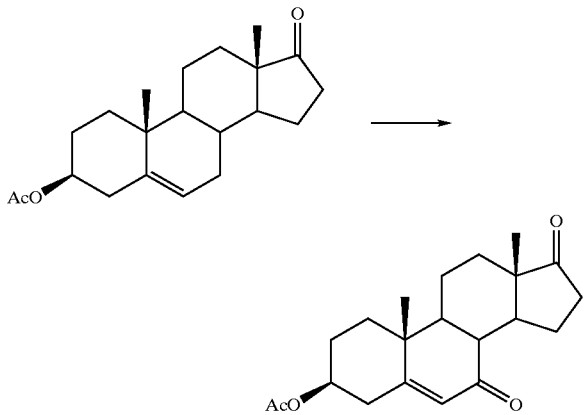

OXIDATION

3β-Acetoxyandrost-5-ene-17-one (DHEAAc) (3.3 grams, 0.01 mol) was dissolved in a mixture of acetonitrile (35 ml), isooctane (30 ml) and t-butyl hydroperoxide (70% aqueous solution, 20 ml). The solution was stirred vigorously at room temperature and sodium periodate (6.42 grams, 0.03 mol) and water (9 ml) added. The reaction mixture was stirred continuously until the reaction had run to completion (15 hours).

SEPARATION

The acetonitrile and isooctane were removed from the reaction mixture under reduced pressure and the resultant residue poured into a mixture of ice water (200 ml) and dichloromethane (20 ml). The dichloromethane layer was separated, washed with water, and distilled to give crude 7-oxo-DHEAAc. The crude 7-oxo-DHEAAc was dissolved in ether and held at −20° C. for 2 hours to form a crystalline precipitate. The crystalline material was filtered, washed with cold ether, and dried under suction to yield 7-oxo-DHEAAc (1.9 grams).

SECONDARY RECOVERY

The ethereal mother liquor was added to a solution of sodium sulfite (15% aqueous solution, 100 ml) and stirred for 2 hours at room temperature to decompose any excess t-butyl hydroperoxide. The ether layer was separated, washed twice with water, dried and distilled to produce a crude oily mass. The crude oily mass was chromatographed on silica gel (70–230 mesh) and the product eluted with 25% (v/v) ethyl acetate in hexane to give another 0.35 gram of 7-oxo-DHEAAc.

YIELD

Total combined yield of 7-oxo-DHEAAc was 2.25 grams (65.4%).

PURIFICATION AND CHARACTERIZATION

The 7-oxo-DHEAAc (2.25 grams) was recrystallized from methanol-water (98:2) to yield 1.95 grams (56.6%) of pure crystalline 7-oxo-DHEAAc as white needles having a melting point of 185–186° C.

Example 5

(Oxidation of 3β-Acetoxyandrost-5-ene-17-one (DHEAAc) to 3β-Acetoxyandrost-5-ene-7,17-dione (7-oxo-DHEAAc))

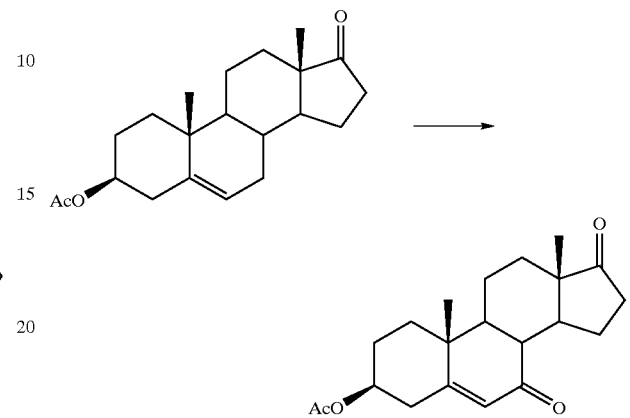

OXIDATION

3β-Acetoxyandrost-5-ene-17-one (DHEAAc) (0.33 gram, 0.001 mol) was dissolved in a mixture of acetone (4 ml), heptane (3.5 ml) and t-butyl hydroperoxide (70% aqueous solution, 2 ml). The solution was stirred vigorously at room temperature and sodium periodate (0.64 gram, 0.003 mol), water (0.5 ml) and pyridine (0.2 ml) was added. The reaction mixture was stirred continuously for 16 hours until the reaction had run to completion.

SEPARATION

The organic solvent was removed from the reaction mixture under reduced pressure and the resultant mass poured into ice water (200 ml) and extracted twice with a mixture of ethyl acetate-hexane (30 ml, 1:1). The combined extracts were stirred with an aqueous sodium bisulfite solution (15% aqueous solution, 100 ml) for 2 hours at room temperature. The organic layer was separated, washed with water, dried and distilled to form a crude material. The crude material was stirred with ether and cooled for 2 hours to produce white crystalline 7-oxo-DHEAAc. The crystalline 7-oxo-DHEAAc was filtered, washed with cold ether and dried to afford 0.18 gram of 7-oxo-DHEAAc.

The filtrate was concentrated and chromatographed on silica gel (70–230 mesh). The product was eluted with ethyl acetate-hexane (1:3) to yield an additional 0.04 gram of 7-oxo-DHEAAc.

YIELD

Total combined yield of 7-oxo-DHEAAc was 0.22 gram (64%).

PURIFICATION AND CHARACTERIZATION

The 7-oxo-DHEAAc (0.22 gram) was recrystallized from ethanol-water to yield 0.19 gram (55.2%) of pure crystalline 7-oxo-DHEAAc as white needles.

Example 6

(Oxidation of 3β-Acetoxyandrost-5-ene-17-one (DHEAAc) to 3β-Acetoxyandrost-5-ene-7,17-dione (7-Oxo-DHEAAc))

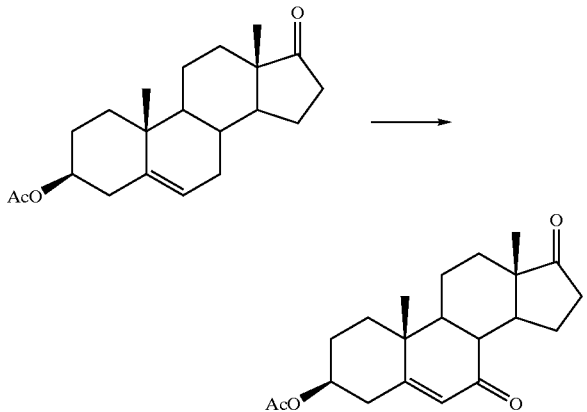

OXIDATION

3β-Acetoxyandrost-5-ene-17-one (DHEAAc) (0.33 gram, 0.001 mol) was dissolved in a mixture of pyridine (3 ml), water (2 ml) and t-butyl hydroperoxide (90% aqueous solution, 2 ml). The solution was stirred vigorously at room temperature and sodium periodate (0.64 gram, 0.003 mol) was added. The reaction mixture was stirred continuously for 8 hours until the reaction had run to completion.

SEPARATION

The reaction mixture was poured into ice water and the oxidation product extracted with ethyl acetate-hexane (1:1). The organic layer was separated, stirred with an aqueous sodium sulfite solution (15% aqueous solution, 10 ml), washed with water, dried and distilled. The crude product was triturated with diethyl ether and held for 4 hours at −20° C. to form a crystalline precipitate. The crystalline material was filtered, washed with ether and dried to yield 0.23 gram of 7-oxo-DHEAAc (66.8%).

YIELD

Total yield of 7-oxo-DHEAAc was 0.23 gram (66.8%).

PURIFICATION AND CHARACTERIZATION

The 7-oxo-DHEAAc (0.23 gram) was recrystallized from acetone-hexane (8:2) to yield 0.21 gram (61%) of pure crystalline 7-oxo-DHEAAc as white needles having a melting point of 183–185° C.

Example 7

(Oxidation of 3β-Acetoxyandrost-5-ene-17-one (DHEAAc) to 3β-Acetoxyandrost-5-ene-7,17-dione (7-Oxo-DHEAAc))

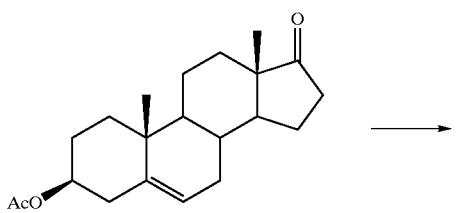

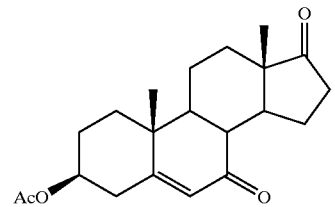

OXIDATION

3β-Acetoxyandrost-5-ene-17-one (DHEAAc) (1.1 grams, 0.0033 mol) was dissolved in a mixture of acetone (18 ml), and t-butyl hydroperoxide (70% aqueous solution, 5.0 ml) and the solution cooled to 0° C. The solution was stirred vigorously and an aqueous solution of ortho periodic acid (0.84 gram, 0.036 mol) dissolved in 2.0 ml of water added to the solution while maintaining the temperature at 0–2° C. to form a first reaction mixture. The first reaction mixture was stirred continuously for 4 hours at 0–2° C., at which time an additional amount of solid periodic acid (0.4 gram, 0.0017 mol) was added to form a second reaction mixture. The second reaction mixture was stirred continuously for 24 hours at 0–2° C.

SEPARATION

To the second reaction mixture was added a 15% solution of sodium sulfite. The mixture was stirred for 1 hour at 10° C. and then poured with stirring into ice water and extracted with ethyl acetate (10 ml). The organic layer was separated, washed with water, dried over magnesium sulfate and stirred with basic alumina (1.0 grams) for 1 hour. The resultant mixture was filtered, concentrated, and on treatment with hexane afford a white crystalline solid which was filtered and dried to yield 0.5 gram of 7-oxo-DHEAAc.

SECONDARY RECOVERY

The organic filtrate was separated, concentrated and the residue chromatographed on silica gel with the product eluted wit 20% (v/v) ethyl acetate in hexane to give another 0.19 gram of 7-oxo-DHEAAc.

YIELD

Total combined yield of 7-oxo-DHEAAc was 0.69 gram (61.06%). The melting point was measured at 184–185° C.

Example 8

(Oxidation of 3β-Acetoxyandrost-5-ene-17-one (DHEAAc) to 3β-Acetoxyandrost-5-ene-7,17-dione (7-Oxo-DHEAAc))

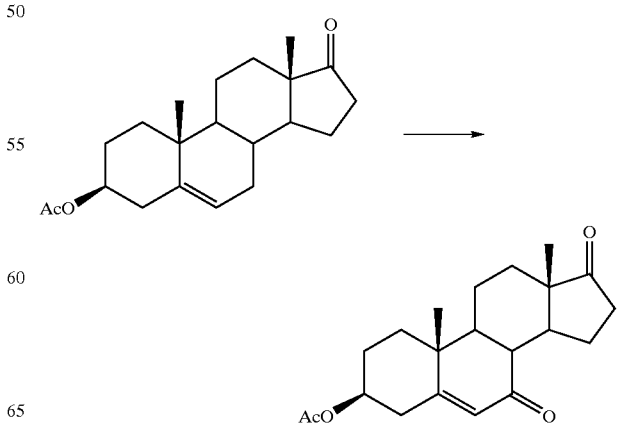

OXIDATION

3β-Acetoxyandrost-5-ene-17-one (DHEAAc) (5.0 grams, 0.015 mol) was dissolved in a mixture of t-butanol (60 ml), t-butyl hydroperoxide (70% aqueous solution, 20 ml), and water (10 ml). The solution was stirred vigorously at room temperature and periodic acid (4.0 grams, 0.017 mol) added in three portions every hour. The resultant reaction mixture was stirred continuously for 16 hours at room temperature.

SEPARATION

To the reaction was added a 15% solution of sodium sulfite (100 ml). The mixture was stirred for 2 hours at 10° C., poured with stirring into ice water and extracted with ethyl acetate (30 ml). The organic layer was separated, washed with water, mixed with methanol (20 ml) and stirred at room temperature wit a 2.5 ml saturated solution of sodium bicarbonate for 2 hours. The resultant solution was diluted with water, concentrated, and the precipitated solid filtered, washed with water, and dried under suction to yield 2.4 grams of 7-oxo-DHEAAc.

SECONDARY RECOVERY

The mother liquor was chromatographed on silica gel (70–230 mesh) with the product eluted with 20% (v/v) ethyl acetate in hexane to give 0.52 gram of pure 7-oxo-DHEAAc.

YIELD

Total combined yield of 7-oxo-DHEAAc was 2.92 grams (56.58%). The melting point was measured at 184–185° C.

Example 9

(Oxidation of 3β-Acetoxyandrost-5-ene-17-one (DHEAAc) to 3β-Acetoxyandrost-5-ene-7,17-dione (7-Oxo-DHEAAc))

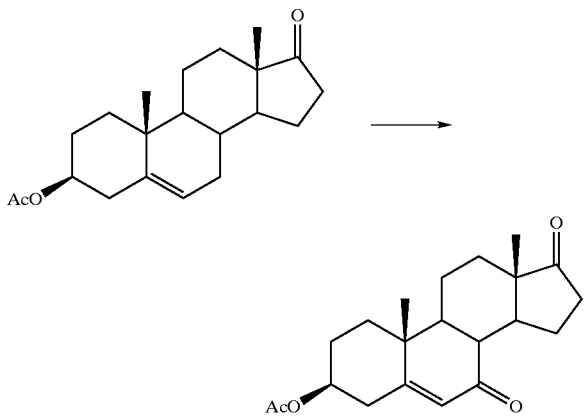

OXIDATION

3β-Acetoxyandrost-5-ene-17-one (DHEAAc) (0.5 gram, 0.015 mol) was dissolved in a mixture of acetone (10 ml) and t-butyl hydroperoxide (70% aqueous solution, 2 ml). The solution was stirred vigorously at room temperature and periodic acid (0.3 gram, 0.013 mol) absorbed on silica gel (0.3 gram) was added portionwise over 4 hours. The resultant reaction mixture was stirred continuously for 24 hours at room temperature until the reaction had run to completion.

SEPARATION

The reaction mixture was filtered on celite, organic solvent removed under reduced pressure, and the resultant mass poured into ice water (20 ml) and extracted twice with a mixture of ethyl acetate-hexane (30 ml, 1:1). The combined extracts were washed with an aqueous sodium bisulfite solution (15% aqueous solution), washed with water, dried and then distilled to form a crude material. The crude material was stirred with ether and cooled for 2 hours to produce a white crystalline product. The crystalline product was filtered, washed with cold water, and dried to give 0.24 gram of 7-oxo-DHEAAc.

SECONDARY RECOVERY

The filtrate was concentrated and chromatographed on silica gel (70–230 mesh) with the product eluted with 33% (v/v) ethyl acetate-hexane to give another 0.06 gram of 7-oxo-DHEAAc.

YIELD

Total combined yield of 7-oxo-DHEAAc was 0.30 gram (58%).

Example 10

(Oxidation of 3β-Ol-androst-5-ene-17-one (DHEA) to 3β-Ol-androst-5-ene-7,17-dione (7-Oxo-DHEA))

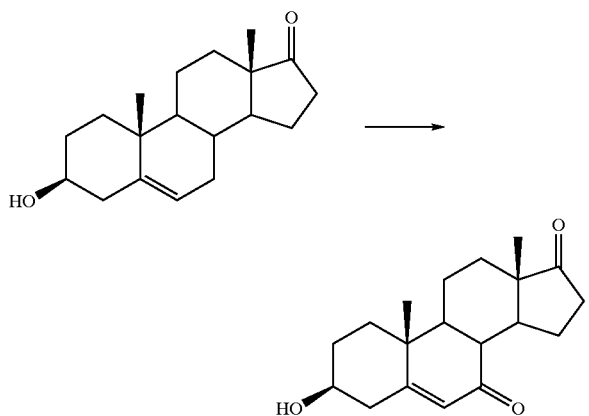

OXIDATION

3β-Ol-androst-5-ene-17-one (DHEA) (1.44 grams, 0.005 mol) was dissolved in a mixture of acetone (10 ml), petroleum-ether (10 ml) and t-butyl hydroperoxide (70% aqueous solution, 10 ml). The solution was stirred vigorously at room temperature and sodium periodate (3.0 grams, 0.014 mol) added. The reaction mixture was stirred continuously until the reaction had run to completion (8 hours).

SEPARATION

The reaction mass was poured into ice water and stirred continuously for 1 hour. The mixture was then cooled for an additional 2 hours at 0–5° C. to form a crystalline precipitate. The crystalline material was filtered under suction, washed with water and then with cold ether, and dried to yield 0.65 gram of 7-oxo-DHEA.

The organic layer of the filtrate was separated from the aqueous layer and washed with an aqueous sodium sulfite solution (10% aqueous solution), aqueous sodium bicarbonate and water. The solvent was removed by a rotary evaporator and the resulting residue chromatographed on a short column of silica gel (70–230 mesh) using hexane-ethyl acetate (60:40) as eluent to yield an additional amount (0.3 gram) of 7-oxo-DHEA.

YIELD

Total combined yield of 7-oxo-DHEA was 0.95 gram (62.9%).

PURIFICATION AND CHARACTERIZATION

The 7-oxo-DHEA (0.95 gram) was recrystallized from methanol to yield 0.8 gram (53%) of pure crystalline 7-oxo-DHEA as white needles having a melting point of 238–240° C. and the following NMR spectrum.

$^1$H NMR (CDCl$_3$, 200 MHz); δ 5.75 (d, J=1.4 Hz, 1H, 6H), 3.68 (m, 1H, 3α-H), 1.23 (s, 3H, 19-CH$_3$), 0.90 (s, 3H, 18-CH$_3$).

Example 11

(Oxidation of 3β-Ol-androst-5-ene-17-one (DHEA) to 3β-Ol-androst-5-ene-7,17-dione (7-Oxo-DHEA))

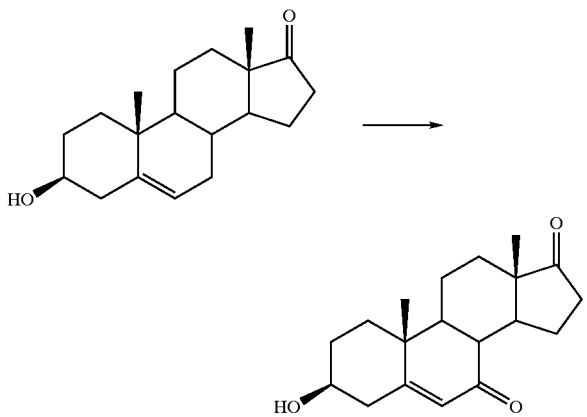

OXIDATION

3β-Ol-androst-5-ene-17-one (DHEA) (2.88 grams, 0.01 mol) was dissolved in a mixture of t-butanol (15 ml) and t-butyl hydroperoxide (70% aqueous solution, 15 ml). The solution was stirred vigorously at room temperature and an aqueous solution of periodic acid (2.3 grams, 0.01 mol in 5 ml of water) was added over 1 hour. The resultant reaction mixture was stirred continuously at room temperature for 16 hours.

SEPARATION

The resultant reaction mixture was poured into ice water and stirred continuously for 1 hour. The mixture was maintained at 0–5° C. for an additional 2 hours to form a crystalline precipitate. The crystalline precipitate was filtered under suction, washed with water, washed with cold ether, and dried to give 1.4 grams of 7-oxo-DHEA.

SECONDARY RECOVERY

The ethereal organic layer from the filtrate was separated, washed with an aqueous sodium sulfite solution (10% aqueous solution0, and then washed with an aqueous sodium bicarbonate solution. The solvent was removed by a rotary evaporator and the resulting residue chromatographed on a short column of silica gel (70–230 mesh) with the product eluted with 40% (v/v) ethyl acetate in hexane to give an additional 0.3 gram of 7-oxo-DHEAAc.

YIELD

Total combined yield of 7-oxo-DHEA was 1.7 grams (56.3%). The melting point was measured at 236–238° C.

Example 12

(Oxidation of 3β,17β-Diacetoxyandrost-5-ene to 3β,17β-Diacetoxyandrost-5-ene-7-one)

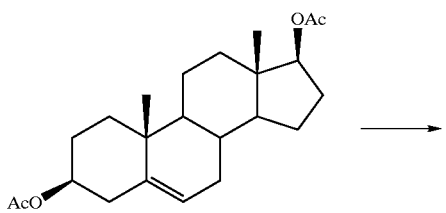

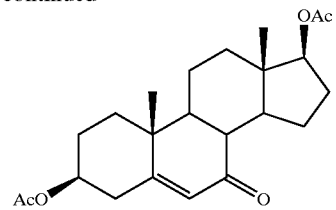

OXIDATION

3β,17β-Diacetoxyandrost-5-ene (1.12 grams, 0.003 mol) was dissolved in a mixture of acetone (12 ml) and t-butyl hydroperoxide (anhydrous, 3M solution in 2,2,4-trimethylpentane, 15 ml). The solution was stirred vigorously at room temperature and sodium periodate (1.92 grams, 0.009 mol) and water (3 ml) added. This biphasic reaction mixture was stirred continuously for 16 hours at room temperature until the reaction had run to completion.

SEPARATION

The solvent was removed under reduced pressure and the resulting residue diluted with dichloromethane (10 ml). The dichloromethane layer was washed thoroughly with water and then stirred with an aqueous sodium sulfite solution (15% aqueous solution, 30 ml) for 2 hours. The organic layer was separated, washed with water, evaporated to dryness, and the resultant crude product dissolved in ether and held for 4 hours at –20° C. to form a crystalline precipitate. The crystalline material was collected under suction, washed with cold ether, and dried to yield 0.76 gram of 3β,17β-diacetoxyandrost-5-ene-7-one.

SECONDARY RECOVERY

The mother liquor was chromatographed on silica gel (70–230 mesh) using ethyl acetate-hexane as eluent to yield an additional amount (0.15 gram) of 3β,17β-diacetoxyandrost-5-ene-7-one having a melting point of 222–224° C.

YIELD

Total combined yield of 3β,17β-diacetoxyandrost-5-ene-7-one was 0.91 gram (78.4%).

CHARACTERIZATION

The 3β,17β-diacetoxyandrost-5-ene-7-one had a melting point of 222–224° C. and the following NMR spectrum.

$^1$H NMR (CDCl$_3$, 200 MHz); δ 5.72 (d, J=1.4 Hz, 1H, 6H), 4.69 (m, 2H, 3α-H & 17α-H), 2.05 (s, 3H, COCH$_3$), 2.045 (s, 3H, COCH$_3$), 1.22 (s, 3H, 19-CH$_3$), 0.81 (s, 3H, 18-CH$_3$).

Example 13

(Oxidation of 3β,17β-Diacetoxyandrost-5-ene to 3β,17β-Diacetoxyandrost-5-ene-7-one)

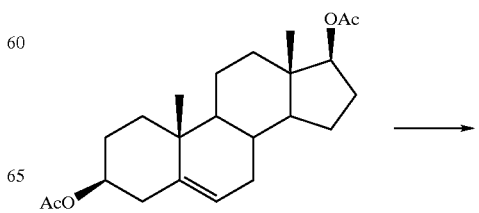

-continued

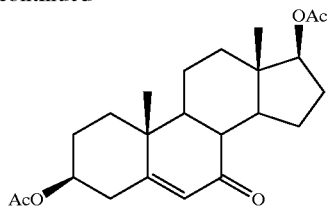

OXIDATION

3β,17β-Diacetoxyandrost-5-ene (1.87 grams, 0.005 mol) was dissolved in a mixture of acetone (20 ml), isooctane (15 ml) and t-butyl hydroperoxide (70% aqueous solution, 10 ml). The mixture was stirred vigorously at room temperature and sodium periodate (3.2 grams, 0.015 mol) and water (3 ml) added. This biphasic reaction mixture was stirred continuously at room temperature until the reaction had run to completion (24 hours).

SEPARATION

The solvent was removed under reduced pressure and the resulting residue diluted with dichloromethane (10 ml). The dichloromethane layer was washed thoroughly with water and then stirred with an aqueous sodium sulfite solution (15% aqueous solution, 30 ml) for 2 hours. The organic layer was separated, washed with water, evaporated to dryness, and the resultant crude product dissolved in ether and held for 4 hours at −20° C. to form a crystalline precipitate. The crystalline material was collected under suction, washed with cold ether, and dried to yield 1.48 grams (76.28%) of 3β,17β-diacetoxyandrost-5-ene-7-one having a melting point of 222–224° C.

SECONDARY RECOVERY

The mother liquor was chromatographed on silica gel (70–230 mesh) using ethyl acetate-hexane as eluent to yield an additional amount (0.07 gram) of pure 3β,17β-diacetoxyandrost-5-ene-7-one.

YIELD

Total combined yield of 3β,17β-diacetoxyandrost-5-ene-7-one was 1.55 grams (79.8%).

Example 14

(Oxidation of 3β-Acetoxycholest-5-ene (CholesterylAc) to 3β-Acetoxycholest-5-ene-7-one (7-Oxo-CholesterylAc))

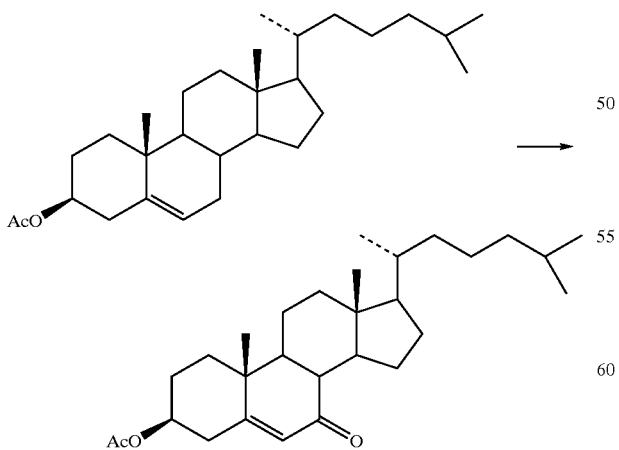

OXIDATION

CholesterylAc (2.14 grams, 0.005 mol) was dissolved in a mixture of acetone (40 ml), isooctane (30 ml) and t-butyl hydroperoxide (70% aqueous solution, 10 ml). The mixture was stirred vigorously at room temperature until clear, and then sodium periodate (3.21 grams, 0.015 mol) and water (7 ml) were added slowly. This biphasic reaction mixture was stirred continuously for 24 hours at room temperature, at which time more than 90% of the starting materials had reacted.

SEPARATION

The acetone was removed under reduced pressure and the residue dissolved in dichloromethane. The resultant organic layer was washed with copious amounts of water and distilled to form a crude material. The crude material was dissolved in methanol (20 ml) and filtered. The filtrate was held for 4 hours at −20° C. to form a crystalline solid. The crystalline material was collected under suction, washed with cold methanol, and dried to yield 1.4 grams of 7-oxo-cholesterylAc having a melting point of 155–156° C.

SECONDARY RECOVERY

The organic filtrate was concentrated, taken up in diethyl ether (20 ml) and stirred with an aqueous sodium sulfite solution (15% aqueous solution, 50 ml) for 2 hours. The ether layer was separated, washed with water, dried, and chromatographed on silica gel (70–230 mesh) using ethyl acetate-hexane (1:9) as eluent to yield an additional amount (0.15 gram) of 7-oxo-cholesterylAc.

YIELD

Total combined yield of 7-oxo-cholesterylAc was 1.55 grams (78.0% based upon 95% conversion).

CHARACTERIZATION

The 7-oxo-cholesterylAc had a melting point of 155–157° C. (melting point for compound listed at 155–156° C. in A. H. Milburn, E. V. Truter and F. P. Woodford, *J. Chem. Soc.*, 1956, 1740) and the following NMR spectrum.

$^1$H NMR (CDCl$_3$, 200 MHz); δ 5.7 (d, J=1.0 Hz, 1H, 6H), 4.72 (m, 1H, 3α-H), 2.05 (s, 3H, COCH$_3$), 1.21 (s, 3H, 19-CH$_3$), 0.91 (d, J=7.2 Hz, 3H, 21CH$_3$), 0.88 & 0.84 (2s, 6H, 26,27-CH$_3$), 0.68 (s, 3H, 18-CH$_3$).

Example 15

(Oxidation of 3β-Acetoxycholest-5-ene (CholesterylAc) to 3β-Acetoxycholest-5-ene-7-one (7-Oxo-CholesterylAc))

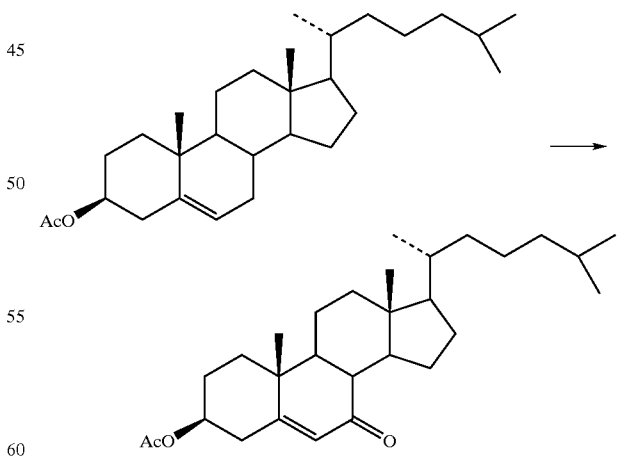

OXIDATION

CholesterylAc (1.07 grams, 0.0025 mol) was dissolved in a mixture of t-butanol (25 ml), and t-butyl hydroperoxide (70% aqueous solution, 10 ml). The solution was stirred vigorously at room temperature until clear, and then aqueous periodic acid solution (1.14 grams, 0.005 mol in 5 ml of water) added slowly over a 2-hour period. The resultant mixture was stirred continuously for 24 hours at room temperature.

SEPARATION

To the reaction mixture was added a 10% aqueous sodium sulfite solution (25 ml) of 1 hour. The reaction mixture was then diluted with 25 ml of cold water and maintained at 0° C. for 2 hours to form a crystalline solid. The crystalline solid was collected under suction, washed with cold methanol, and dried to yield 0.58 gram of 7-oxo-cholesterylAc.

SECONDARY RECOVERY

The aqueous layer was extracted with ethyl acetate and combined with the methanol washings. The solvent was evaporated from the combination and the residue was chromatographed on silica gel (70–230 mesh) with the product eluted with 10% (v/v) ethyl acetate to give 0.11 gram of cholesterylAc followed by (0.15 gram) of 7-oxo-cholesterylAc.

YIELD

Total combined yield of 7-oxo-cholesterylAc was 0.73 gram (73.7% based upon 90% conversion). The melting point was measured at 155–157° C.

Example 16

(Oxidation of 3β-Acetoxy-17,17-ethylenedioxyandrost-5-ene to 3β-Acetoxy-17,17-ethylenedioxyandrost-5-ene-7-one)

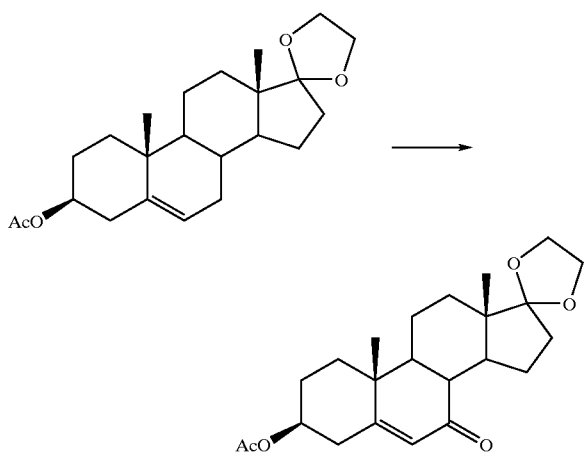

OXIDATION

3β-Acetoxy-17,17-ethylenedioxyandrost-5-ene (0.374 gram, 0.001 mol) was dissolved in a mixture of acetone (3.5 ml) and heptane (3.5 ml). Aqueous t-butyl hydroperoxide (70% aqueous solution, 2 ml) was added to the solution and the resultant solution stirred at room temperature for 15 minutes, after which sodium periodate (0.65 gram, 0.003 mol), water (0.9 ml) and sodium bicarbonate (0.055 gram) were added in succession. This reaction mixture was stirred continuously at room temperature until the reaction had run to completion (14 hours).

SEPARATION

The reaction mixture was diluted with ethyl acetate (10 ml) and then sequentially washed with excess water, twice with an aqueous sodium sulfite solution (15% aqueous solution), and water. Evaporation of the solvent yielded 0.31 gram of a white solid having a melting point of 180–182° C.

PURIFICATION AND CHARACTERIZATION

The 3β-acetoxy-17,17-ethylenedioxyandrost-5-ene-7-one was recrystallized from methanol to yield 0.26 gram (67.0%) of pure crystalline 3β-acetoxy-17,17-ethylenedioxyandrost-5-ene-7-one as white needles having a melting point of 182–183° C. (melting point for compound listed in the literature as 175–177° C. in Fieser, L. R., JACS 76, 1945, (1954)) and the following NMR spectrum.

$^1$H NMR (CDCl$_3$, 200 MHz); δ 5.7 (d, J=1.4 Hz, 6H), 4.7 (m, 1H, 3α-H), 3.87 (m, 6H, CH$_2$-ketal), 2.06 (s, 3H, COCH$_3$), 1.21 (s, 3H, 19-CH$_3$), 0.87 (s, 3H, 18-CH$_3$).

Example 17

(Oxidation of Diphenyl Methane to Benzophenone)

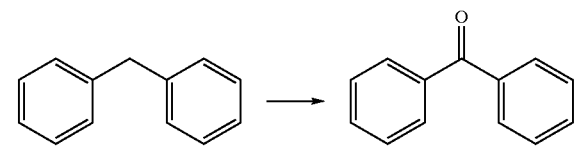

OXIDATION

Diphenyl methane (3.36 grams, 0.02 mol) was dissolved in a mixture of acetone (30 ml), petroleum ether (30 ml), t-butyl hydroperoxide (70% aqueous solution, 20 ml) and water (9 ml). The mixture was stirred vigorously at room temperature and sodium periodate (6.42 grams, 0.03 mol) added. This biphasic reaction mixture was stirred continuously for 48 hours at room temperature, at which time 90% of the starting materials had reacted.

SEPARATION

The solvent was removed by evaporation under water pump suction. The resulting residue was stirred with an aqueous sodium sulfite solution (15% aqueous solution, 100 ml) for 2 hours. The resulting product was extracted with diethyl ether and washed twice with water.

The organic phase was dried over magnesium sulfate and evaporated. The residue was chromatographed on a column of silica gel (70–230 mesh) and eluted with ethyl acetate (0–3% (v/v)) in hexane. The fractions eluted with hexane were combined and distilled to yield 0.30 gram of unreacted diphenyl methane. The ethyl acetate-hexane fractions were combined and evaporated to yield benzophenone as a white oil (3.0 grams).

YIELD

Total yield of benzophenone was 3.0 grams (92.4% based upon 90% conversion).

CHARACTERIZATION

The benzophenone had the following NMR spectrum.

$^1$H NMR (CDCl$_3$, 200 MHz); δ 7.43–7.64 and 7.78–7.84 (m, 10H, ArH).

Example 18

(Oxidation of Diphenyl Methane to Benzophenone)

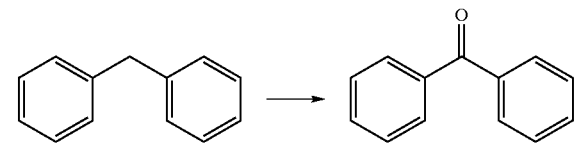

OXIDATION

Diphenyl methane (1.68 grams, 0.01 mol) was dissolved in a mixture of acetone (50 ml), t-butyl hydroperoxide (70% aqueous solution, 13 ml) and water (10 ml). The solution was stirred vigorously at room temperature and sodium periodic acid (4.0 grams, 0.0175 mol) was added over a 2-hour period. This resultant reaction mixture was stirred continuously for 24 hours at room temperature.

SEPARATION

Solvent was removed from the reacted mixture by evaporation under water pump suction. An aqueous sodium sulfite solution (15% aqueous solution, 100 ml) was added to the resulting reside and the mixture stirred for 2 hours. Product was then extracted with isopropyl ether and washed twice with water.

The organic phase was dried over magnesium sulfate and evaporated. The resultant residue was chromatographed on a column of silica gel (70–230 mesh) and eluted with (i) hexane, and (ii) 3% (v/v) ethyl acetate in hexane. The fractions eluted with hexane were combined and distilled to yield 0.17 gram of unreacted diphenyl methane. The fractions eluted with ethyl acetate-hexane were combined and evaporated to yield 1.56 grams of benzophenone as a white oil.

YIELD

Total yield of benzophenone was 1.56 grams (95% based upon 90% conversion).

Example 19

(Oxidation of Fluorene to Fluorenone)

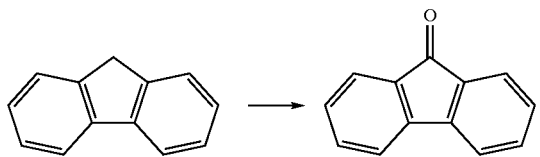

OXIDATION

Fluorene (1.66 grams, 0.01 mol) was dissolved in a mixture of acetone (40 ml), heptane (30 ml), t-butyl hydroperoxide (70% aqueous solution, 20 ml) and water (4 ml). The resultant solution was stirred at room temperature for 15 minutes, after which sodium periodate (4.26 grams, 0.02 mol) was added. This reaction mixture was stirred continuously at room temperature until the reaction had run to completion (16 hours).

SEPARATION

The solvent was removed under vacuum and diethyl ether (20 ml) added to the residue. The organic layer was separated, washed with copious amounts of water and then stirred with an aqueous sodium sulfite solution (15% aqueous solution, 100 ml) for 2 hours at room temperature. The ether layer was separated, washed with water, dried and distilled to yield fluorenone. The fluorenone was dissolved in ethanol (95%) and held for 2 hours at −10° C. to form a crystalline solid. The pale yellow crystals of fluorenone were filtered washed with cold ethanol, dried under suction and then dried in a vacuum desiccator for 2 hours to yield fluorenone (1.71 grams)

YIELD

Total yield of fluorenone was 1.71 grams (95.0%).

CHARACTERIZATION

The fluorenone had a melting point of 82–84° C. (melting point for compound listed at 82–85° C. in the Aldrich Catalogue) and had the following NMR spectrum.

$^1$H NMR (CDCl$_3$, 200 MHz): δ 7.67 (t), 7.64 (t), 7.5 (m) and 7.29 (m) 8H, ArH Example 20

Oxidation of Fluorene to Fluorenone

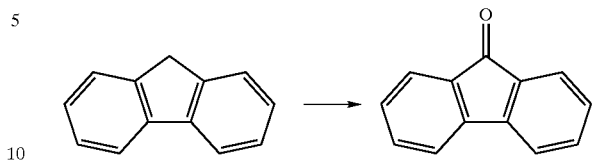

OXIDATION

Fluorene (1.66 grams, 0.01 mol) was dissolved in a mixture of acetone (50 ml), t-butyl hydroperoxide (70% aqueous solution, 13 ml) and water (10 ml). The resultant solution was stirred at room temperature for 15 minutes, after which periodic acid (4.0 grams, 0.0175 mol) was added over a 2-hour period. This reaction mixture was stirred continuously at room temperature until the reaction had run to completion (24 hours).

SEPARATION

The reaction mixture was concentrated under vacuum and an aqueous sodium sulfite solution (15% aqueous solution, 100 ml) added over a 2-hour period at room temperature. The resultant product was extracted with isopropyl ether, washed with water, dried and distilled to yield fluorenone. The fluorenone was dissolved in ethanol (95%) and held for 2 hours at −10° C. to form a pale yellow crystalline solid. The crystals were filtered, washed with cold ethanol, dried under suction and then dried in a vacuum desiccator for 2 hours to yield 1.7 grams of fluorenone.

YIELD

Total yield of fluorenone was 1.71 grams (94.4%).

CHARACTERIZATION

The fluorenone had a melting point of 82–84° C.

Example 21

Oxidation of Methyl 9-octadecenoate to a Mixture of the Isomers Methyl 8-oxo-9-octadecenoate and Methyl 11-oxo-9-octadecenoate

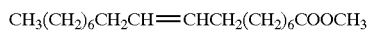
CH$_3$(CH$_2$)$_6$CH$_2$CH=CHCH$_2$(CH$_2$)$_6$COOCH$_3$

CH$_3$(CH$_2$)$_6$COCH=CHCH$_2$(CH$_2$)$_6$COOCH$_3$

+
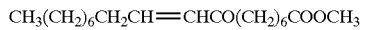
CH$_3$(CH$_2$)$_6$CH$_2$CH=CHCO(CH$_2$)$_6$COOCH$_3$

OXIDATION

Methyl oleate (1.1 grams, 0.0029 mol) was dissolved in a mixture of acetone (3.2 ml), heptane (3.0 ml), t-butyl hydroperoxide (70% aqueous solution, 3 ml) and water (0.45 ml). The resultant solution was stirred at room temperature and sodium periodate (0.94 gram, 0.0044 mol) was added. This reaction mixture was stirred continuously for 36 hours at room temperature then quenched with water, at which time 58% of the starting materials had reacted

SEPARATION

The quenched reaction mixture was extracted with diethyl ether and sequentially washed with water, an aqueous sodium sulfite solution (15% aqueous solution), and water. The organic layer was dried over magnesium sulfate and evaporated under reduced pressure. The resulting oily residue was chromatographed on a column of silica gel (70–230 mesh) and eluted with ethyl acetate (0–5% (v/v)) in petroleum ether. The fractions eluted with pure petroleum ether were combined and distilled to yield 0.46 gram (41.8%) of unreacted methyl oleate. The fractions eluted with 5% (v/v) ethyl acetate in petroleum ether were combined and evaporated to yield 0.30 gram (45.0%) of a white oil. The white oil was found to be a 1:1 mixture of methyl 11-oxo-9-octadecenoate and methyl-8-oxo-9-octadecenoate as shown by $^1$H NMR and TLC (TLC plates were impregnated with boric acid and silver nitrate, dried and activated at 120° C. for 4 hours before use. A mixture of 10% (v/v) ether in petroleum ether was used as a mobile phase.).

YIELD

Total yield of product was 0.30 gram (45% based upon 58% conversion).

CHARACTERIZATION

The product had the following NMR spectrum.

$^1$H NMR (CDCl$_3$, 200 MHz): δ 6.83 (dtd, J=15.8, 6.6 and 2.0 Hz, 1H, olefinic), 6.12, 6.05 (dt, J=15.6 and 1.4 Hz, 1H, olefinic), 3.67 (s, 3H, OCH$_3$), 2.51 (t, 2H, CH$_2$), 2.32 (t, 2H, CH$_2$), 0.89 (t, 3H, CH$_3$).

Example 22

Oxidation of R(+) α-Pinene to R(+) α-Verbenone

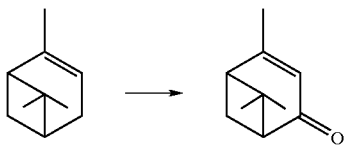

OXIDATION

R(+) α-pinene (2.8 grams, 0.0186 mol) was dissolved in a mixture of acetone (32 ml), pyridine (3 ml), and t-butyl hydroperoxide (70% aqueous solution, 20 ml). The resultant solution was stirred at room temperature and sodium periodate (6.5 grams, 0.03 mol) and water (9.0 ml) added. This reaction mixture was stirred continuously at room temperature until the reaction had run to completion (16 hours).

SEPARATION

Acetone was removed from the reaction mixture by evaporation, the residue diluted with ether (20 ml) and the ether layer washed with water. The organic layer was stirred with a sodium sulfite solution (15% aqueous solution, 100 ml) for 2 hours at room temperature, washed with water and evaporated to form a crude product.

The crude product was chromatographed on a silica gel column (70–230 mesh). The product was eluted with ethyl acetate (5% (v/v)) in hexane to yield pure (R+) α-verbenone (0.45 gram).

YIELD

Total yield of purified R(+) α-verbenone (95% purity, HPLC at 254 nm) was 0.45 gram (16%).

CHARACTERIZATION

The R(+) α-verbenone had the following NMR spectrum.

$^1$H NMR (CDCl$_3$, 200 MHz): δ 5.73 (m, 1H, 3H, olefinic-H), 2.01 (d, J=1.4 Hz, 3H, CH$_3$). 1.5 (s, 3H, CH$_3$), 1.01 (s, 3H, CH$_3$).

Example 23

Oxidation of R(+) α-Pinene to R(+) α-Verbenone

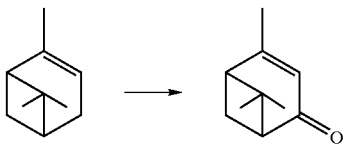

OXIDATION

R(+) α-pinene (1.36 grams, 0.01 mol) was dissolved in a mixture of t-butanol (15 ml), pyridine (3 ml), water (5 ml) and t-butyl hydroperoxide (70% aqueous solution, 13 ml). The resultant solution was stirred at room temperature and periodic acid (3.42 grams, 0.015 mol) added over a 2-hour period. This resultant mixture was stirred continuously for 24 hours.

SEPARATION

Acetone was removed from the reaction mixture by evaporation. A sodium solution (15% aqueous solution, 100 ml) was added to the residue and the resultant mixture stirred for 2 hours at room temperature. Product was extracted with isopropyl ether and the ethereal layer washed with water and evaporated to form a crude product.

The crude product was chromatographed on a silica gel column (70–230 mesh) with the product eluted with 5% (v/v) ethyl acetate in hexane to give 0.27 gram pure R(+) α-verbenone.

YIELD

Total yield of purified R(+) α-verbenone was 0.27 gram (18%).

Example 24

Oxidation of 3β-Acetoxyandrost-5-ene-17-one (DHEAAc) to 3β-Acetoxyandrost-5-ene-7,17-dione (7-oxo-DHEAAc

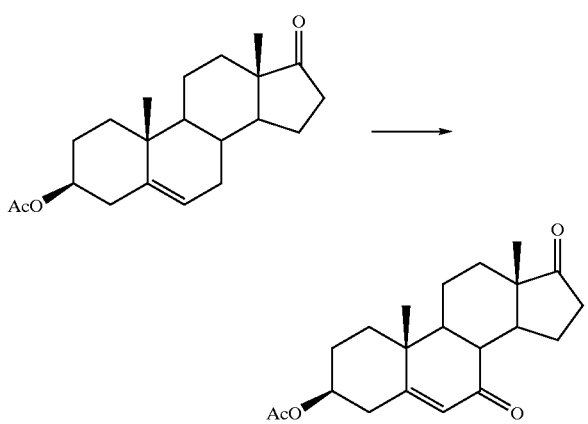

OXIDATION

3β-Acetoxyandrost-5-ene-17-one (DHEAAc) (5.0 grams, 0.015 mol) was dissolved in a mixture of t-butanol (40 ml), t-butyl hydroperoxide (70% aqueous solution, 20 ml) and water (20 ml) at 35° C. The resultant solution was heated to 40° C. and stirred vigorously. Sodium periodate (8.0 grams, 0.037 mol) was added to the solution in three portions of 4.0, 2.0 and 2.0 grams at 30 minutes intervals. After 3 hours of continuous stirring at 35° C., isopropyl ether (15 ml) was added and the reaction mixture was stirred at the same temperature for another 3 hours.

SEPARATION

The reaction mixture was cooled and stirred with a 10% aqueous sodium sulfite solution (150 ml) at 10° C. over a 2-hour period. The reaction mixture was then maintained at 0–5° C. for 12 hours to produce a white solid precipitate. The precipitate was filtered, washed with water, washed twice with isopropyl ether (10 ml), and dried under vacuum to yield 2.8 grams (53.7%) of technical 7-oxo-DHEAAc. The technical 7-oxo-DHEAAc was crystallized from methanol to afford pure 7-oxo-DHEAAc (2.5 grams). The melting point was measured at 184–185° C.

SECONDARY RECOVERY

The aqueous layer was extracted with ethyl acetate and the organic layer washed with water, dried and the solvent removed under vacuum to produce a crude product. The crude product was mixed with the crystallization filtrate and chromatographed on silica gel (70–230 mesh) with the product eluted with 20% ethyl acetate in hexane to give 0.72 gram of pure 7-oxoDHEAAc.

YIELD

Total combined yield of 7-oxo-DHEAAc was 3.22 grams (61.8%). The melting point was measured at 184–185° C.

SIDE PRODUCTS

Analysis of the reaction mixture indicated that the contaminant 3β-acetoxyandrost-5-ene-4,7,17-trione was not formed. Without intending to be unduly limited thereby it is believed that the short reaction time is responsible for the lack of this contaminant.

Example 25

Oxidation of 3β-Acetoxyandrost-5-ene-17-one (DHEAAc) to 3β-Acetoxyandrost-5-ene-7,17-dione (7-oxo-DHEAAc

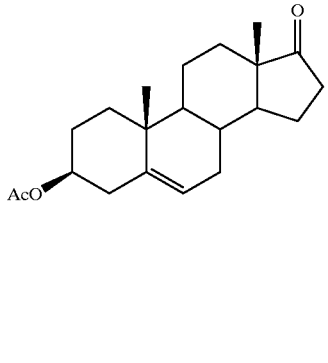

OXIDATION

In to a pressure reaction vessel was placed 3β-Acetoxyandrost-5-ene-17-one (DHEAAc) (3.3 grams, 0.01 mol) and a mixture of t-butanol (45 ml), t-butyl hydroperoxide (70% aqueous solution, 15 ml) and water (15 ml). Sodium periodate (5.35 grams, 0.025 mol) was added to the resultant solution and the vessel sealed under an air pressure of 3 atmospheres (45 psi). The pressurized reaction mixture was stirred continuously for 24 hours at room temperature.

SEPARATION

The reaction mixture was concentrated under reduced pressure at 30° C. to one-third its volume and then a 15% aqueous sodium sulfite solution (100 ml) at 10° C. for over a 2-hour period. The resultant mixture was poured into a mixture of ice water (200 ml) and isopropyl ether (10 ml). The resultant solution was stirred for 30 minutes, cooled to 0–5° C. and maintained at the temperature for 2 hours to form a white precipitate. The precipitate was filtered, washed with water, washed twice with isopropyl ether (5 ml) and dried under vacuum to yield 2.35 grams (68.3%) of technical 7-oxo-DHEAAc.

PURIFICATION

The technical grade 7-oxo-DHEAAc was dissolved in methanol-ethyl acetate (35 ml, 4:3) and a freshly prepared saturated aqueous solution of sodium bicarbonate (2.5 ml) added. The resultant solution was stirred at room temperature for 2 hours, concentrated to half of its original volume under vacuum at 20° C., and dilute with water (15 ml). The diluted solution was cooled to 0° C. and maintained at the temperature for 2 hours to form white crystalline 7-oxo-DHEAAc, The 7-oxo-DHEAAc was filtered, washed with cold methanol, and dried to yield 2.115 grams (61.5%) of pure white 7-oxo-DHEAAc.

SECONDARY RECOVERY

The aqueous layer and the purification filtrate were combined and extracted with ethyl acetate. The resultant organic layer was washed with water, dried and the solvent removed under vacuum. The resultant crude product was chromatographed on silica gel (70–230 mesh) with the product eluted with 20% (v/v) ethyl acetate in hexane to give 0.42 gram of pure 7-oxo-DHEAAc.

YIELD

Total combined yield of 7-oxo-DHEAAc was 2.635 g (76.6%) with a melting point of 184–185° C.

SIDE PRODUCTS

Analysis of the reaction indicated that the final product contained smaller amounts of the various contaminants reference in Example 1, relative to the amounts observed when the process was conducted at ambient temperatures and pressures as in Example 1.

Example 26

Oxidation of 3β-Acetoxyandrost-5-ene-17-one (DHEAAc) to 3β-Acetoxyandrost-5-ene-7,17-dione (7-oxo-DHEAAc

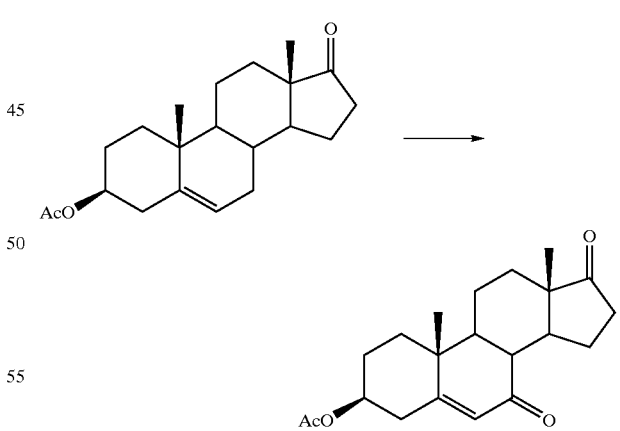

OXIDATION

In to a pressure reaction vessel was placed 3β-Acetoxyandrost-5-ene-17-one (DHEAAc) (3.3 grams, 0.01 mol) and a mixture of t-butanol (45 ml), t-butyl hydroperoxide (70% aqueous solution, 15 ml) and water (15 ml). Sodium periodate (4.28 grams, 0.02 mol) was added to the resultant solution and the vessel sealed under a nitrogen induced pressure of 100 psi. The pressurized reaction mixture was maintained at 35° C., and stirred continuously for 9 hours except for an initial 90 minute temperature spike up to 57° C. before the temperature could be stabilized at 35° C.

SEPARATION

An aqueous sodium sulfite solution (15% aqueous solution, 100 ml) was added to the reaction mixture at 10° C. over a 2-hour period. The resultant mixture was poured into a mixture of ice water (100 ml) and ethyl acetate (30 ml), and stirred for 30 minutes. The resultant organic layer was isolated (85 ml), washed with half brine solution, dried and solvent removed under vacuum to yield technical 7-oxo-DHEAAc.

PURIFICATION

The above technical grade 7-oxo-DHEAAc was dissolved in acetone-petroleum ether (40 ml, 1:1) and stirred with basic alumina (approximately 5 grams), for 2 hours at room temperature. The solution was filtered, the organic solvent distilled off, and the resultant crude solid heated and dissolved in methanol (30 ml). Upon cooling white crystalline 7-oxo-DHEAAc (1.7 grams, 49.9%) was formed.

SECONDARY RECOVERY

The mother liquor was chromatographed on silica gel (70–230 mesh) with the product eluted with 20% (v/v) ethyl acetate in hexane to give 0.55 gram of pure 7-oxo-DHEAAc.

YIELD

Total combined yield of 7-oxo-DHEAAc was 2.25 grams (65.4%) with a melting point of 184–185° C.

What is claimed is:

1. A method to oxidize an allylic compound, comprising:
   (1) contacting the allylic compound, a metal periodate, periodic acid, and an alkyl hydroperoxide to obtain a mixture;
   (2) increasing the pressure on the mixture to obtain a pressurized mixture; and
   (3) optionally changing the temperature of the pressurized mixture.

2. The method of claim 1 wherein the allylic compound is a steroid.

3. The method of claim 1, wherein said mixture further comprises a solvent system selected from the group consisting of water; a water miscible organic solvent and water; and a water immiscible organic solvent, a water miscible organic solvent and water.

4. The method of claim 3, wherein said alkyl hydroperoxide is tert-butyl hydroperoxide.

5. The method of claim 3, wherein said temperature is increased.

6. A method to oxidize an allylic compound, comprising:
   (1) contacting the allylic compound, a metal periodate, periodic acid, and an alkyl hydroperoxide to obtain a mixture;
   (2) changing the temperature of the mixture; and
   (3) increasing the pressure on the mixture to obtain a pressurized mixture.

7. The method of claim 6 wherein the allylic compound is a steroid.

8. The method of claim 6, wherein said mixture further comprises a solvent system selected from the group consisting of water; a water miscible organic solvent and water; and a water immiscible organic solvent, a water miscible organic solvent and water.

9. The method of claim 8, wherein said alkyl hydroperoxide is tert-butyl hydroperoxide.

10. The method of claim 8, wherein said temperature is increased.

11. A method to oxidize an allylic compound, comprising:
   (1) contacting the allylic compound with reagents consisting essentially of a metal periodate and an alkyl hydroperoxide to obtain a mixture;
   (2) increasing the pressure on the mixture to obtain a pressurized mixture; and
   (3) optionally changing the temperature of the pressurized mixture.

12. The method of claim 11, wherein the allylic compound is a steroid.

13. The method of claim 12, wherein the steroid is a $\Delta^5$ androstene.

14. The method of claim 11, wherein the allylic compound is an isoprenoid.

15. The method of claim 13, wherein the $\Delta^5$ androstene is dehydroepiandrosterone.

16. The method of claim 11, wherein said mixture further comprises a solvent system selected from the group consisting of water; a water miscible organic solvent and water; and a water immiscible organic solvent, a water miscible organic solvent and water.

17. The method of claim 16, wherein said alkyl hydroperoxide is tert-butyl hydroperoxide.

18. The method of claim 16, wherein said temperature is increased.

19. A method to oxidize an allylic compound, comprising:
   (1) contacting the allylic compound, periodic acid, and an alkyl hydroperoxide to obtain a mixture;
   (2) increasing the pressure on the mixture to obtain a pressurized mixture; and
   (3) optionally changing the temperature of the pressurized mixture.

20. The method of claim 19, wherein the allylic compound is a steroid.

21. The method of claim 20, wherein the steroid is a $\Delta^5$ androstene.

22. The method of claim 19, wherein the allylic compound is an isoprenoid.

23. The method of claim 21, wherein the $\Delta^5$ androstene is dehydroepiandrosterone.

24. The method of claim 19, wherein said mixture further comprises a solvent system selected from the group consisting of water; a water miscible organic solvent and water; and a water immiscible organic solvent, a water miscible organic solvent and water.

25. The method of claim 24, wherein said alkyl hydroperoxide is tert-butyl hydroperoxide.

26. The method of claim 24, wherein said temperature is increased.

27. A method to oxidize an allylic compound, comprising
   (1) contacting the allylic compound with reagents consisting essentially of a metal periodate and an alkyl hydroperoxide to obtain a mixture;
   (2) changing the temperature of the mixture; and
   (3) optionally increasing the pressure on the mixture to obtain a pressurized mixture.

28. The method of claim 27, wherein the allylic compound is a steroid.

29. The method of claim 28, wherein the steroid is a $\Delta^5$ androstene.

30. The method of claim 27, wherein the allylic compound is an isoprenoid.

31. The method of claim 29, wherein the $\Delta^5$ androstene is dehydroepiandrosterone.

32. The method of claim 27, wherein said mixture further comprises a solvent system selected from the group consisting of water; a water miscible organic solvent and water; and a water immiscible organic solvent, a water miscible organic solvent and water.

33. The method of claim 32, wherein said alkyl hydroperoxide is tert-butyl hydroperoxide.

34. The method of claim 32, wherein said temperature is increased.

35. A method to oxidize an allylic compound, comprising:
    (1) contacting the allylic compound, periodic acid, and an alkyl hydroperoxide to obtain a mixture;
    (2) changing the temperature of the mixture; and
    (3) optionally increasing the pressure on the mixture to obtain a pressurized mixture.

36. The method of claim 35, wherein the allylic compound is a steroid.

37. The method of claim 36, wherein the steroid is a $\Delta^5$ androstene.

38. The method of claim 35, wherein the allylic compound is an isoprenoid.

39. The method of claim 38, wherein the $\Delta^5$ androstene is dehydroepiandrosterone.

40. The method of claim 35, wherein said mixture further comprises a solvent system selected from the group consisting of water; a water miscible organic solvent and water; and a water immiscible organic solvent, a water miscible organic solvent and water.

41. The method of claim 40, wherein said alkyl hydroperoxide is tert-butyl hydroperoxide.

42. The method of claim 40, wherein said temperature is increased.

* * * * *